(12) United States Patent
Nakano (10) Patent No.: US 7,354,751 B2
(45) Date of Patent: Apr. 8, 2008

(54) ALCOHOL DEHYDROGENASE GENE OF ACETIC ACID BACTERIUM

(75) Inventor: Shigeru Nakano, Aichi (JP)

(73) Assignee: Mitsukan Group Corporation, Handa-Shi (JP)

( * ) Notice: Subject to any disclaimer, the term of this patent is extended or adjusted under 35 U.S.C. 154(b) by 104 days.

(21) Appl. No.: 10/548,486

(22) PCT Filed: Feb. 17, 2004

(86) PCT No.: PCT/JP2004/001732

§ 371 (c)(1),
(2), (4) Date: Sep. 9, 2005

(87) PCT Pub. No.: WO2004/081216

PCT Pub. Date: Sep. 23, 2004

(65) Prior Publication Data

US 2007/0026104 A1   Feb. 1, 2007

(30) Foreign Application Priority Data

Mar. 12, 2003   (JP) .............................. 2003-066697

(51) Int. Cl.
- C07H 21/04 (2006.01)
- C12P 21/06 (2006.01)
- C12N 9/02 (2006.01)
- C12N 1/21 (2006.01)

(52) U.S. Cl. .................. 435/189; 435/69.1; 435/6; 435/252.3; 435/471; 536/23.2

(58) Field of Classification Search ............... 435/140, 435/189
See application file for complete search history.

(56) References Cited

U.S. PATENT DOCUMENTS

| 5,914,257 A | 6/1999 | Fukaya et al. |
| 2002/0081677 A1 * | 6/2002 | Javed et al. ................ 435/161 |

FOREIGN PATENT DOCUMENTS

| CN | 2437691 Y | 7/2001 |
| JP | 60-9488 A | 1/1985 |
| JP | 60-9489 A | 1/1985 |
| JP | 61-58584 A | 3/1986 |
| JP | 61-205475 A | 9/1986 |
| JP | 2000-102393 A | 4/2000 |
| JP | 2005-110597 A | 4/2005 |

OTHER PUBLICATIONS

Whisstock, et al. Quarterly Rev. Biophy. 2003, 36, pp. 307-340.*
Tamaki, T. et al., J. Biochem., 1989, vol. 106, pp. 541 to 544.
Adachi, Kazuo, Vitamin, 2002, vol. 76, No. 2, pp. 65 to 77.
Tamaki, T. et al., Biochimica et Biophysica Acta, vol. 1088, pp. 292-300, 1991.
Fukaya et al., Applied and Environmental Microbiology, vol. 55, pp. 171-176, 1989.
Okumura et al., Agricultural and Biological Chemistry, vol. 52, pp. 3125-3129, 1988.
Fukaya et al., Agricultural and Biological Chemistry, vol. 49, pp. 2091-2097, 1985.
Tayama et al., Bioscience, Biotechnology and Biochemistry, vol. 58, pp. 974-975, 1994.
Tsigos et al., European Journal of Biochemistry, vol. 254, pp. 356-362, 1998.
Ameyama et al., Methods in Enzymology, vol. 89, pp. 450-457, 1982.
Ameyama et al., Methods in Enzymology, vol. 89, pp. 491-496, 1982.
Fujiwara et al., Cellulose, pp. 153-158, 1989.
Sokollek et al., Journal of Biotechnology, vol. 60, No. 3, pp. 195-206, (Feb. 26, 1998).
Schüller et al., International Journal of Systematic and Evolutionary Microbiology, vol. 50, No. 6, pp. 2013-2020, (2000).
Kick-Raack et al., PEP Talk, Pesticide Education Program, vol. 6, Issue 8, pp. 1-4, (Aug. 2002).

* cited by examiner

*Primary Examiner*—Ponnathapu Achutamurthy
*Assistant Examiner*—Md Younus Meah
(74) *Attorney, Agent, or Firm*—Birch, Stewart, Kolasch & Birch, LLP (57) ABSTRACT

A novel gene having a function of improving acetic acid fermentation in practical level was cloned from a practical acetic acid bacterium belonging to the genus *Gluconacetobacter* by a method for obtaining a gene having a growth-promoting function in acetic acid-containing medium from the chromosomal DNA library of the acetic acid bacterium. It was made possible to significantly shorten the growth induction period and significantly improve the acetic acid fermentation rate of transformants obtained by introducing the gene into acetic acid bacteria, when such transformants are cultured in the presence of ethanol.

7 Claims, 2 Drawing Sheets

| | | |
|---|---|---|
| MetAlaGlyLysMetLysAlaAlaValVal | ArgGluPheGlyLysProLeuThrIleGlu | 20 |
| GluLeuAspIleProGlnIleAsnThrAsn | GlnIleLeuValLysValAspAlaCysGly | 40 |
| ValCysHisThrAspLeuHisAlaAlaArg | GlyAspTrpProThrLysProArgProPro | 60 |
| PheIleProGlyHisGluGlyIleGlyHis | ValValGluValGlySerAsnValAsnTrp | 80 |
| IleLysThrGlyAspValValGlyValPro | TrpLeuTyrSerAlaCysGlyHisCysGlu | 100 |
| HisCysLeuGlyGlyTrpGluThrLeuCys | GluLysGlnGluAspThrGlyTyrSerVal | 120 |
| AsnGlyCysPheAlaGluTyrValValAla | AspProAsnTyrValAlaHisLeuProLys | 140 |
| AspIleAspProIleLysThrAlaProVal | LeuCysAlaGlyLeuThrValTyrLysGly | 160 |
| LeuLysMetThrAspThrArgAlaGlyGlu | TrpValAlaIleSerGlyAlaGlyGlyLeu | 180 |
| GlyGlnMetAlaIleGlnTyrAlaValAla | MetGlyLeuAsnValAlaAlaValAspIle | 200 |
| SerAspGluLysLeuGluGluAlaArgLys | LeuGlyAlaArgValThrValAsnAlaLeu | 220 |
| LysGlnAspProValAlaTyrIleArgGlu | GlnThrGlyGlyThrHisGlyValLeuVal | 240 |
| ThrAlaValSerAspLysAlaPheSerGln | AlaValGlyTyrAlaArgArgGlyGlyThr | 260 |
| ValValLeuAsnGlyLeuProProGlyAsp | PheProLeuSerIlePheAspMetValMet | 280 |
| AsnGlyThrThrValArgGlySerIleVal | GlyThrArgLeuAspMetIleGluAlaMet | 300 |
| SerPhePheThrAspGlyLysValThrThr | ValValSerThrAspLysLeuGluAsnIle | 320 |
| AsnThrIlePheAspAsnLeuGlnHisGly | ArgValLysGlyArgValValLeuAspPhe | 340 |
| ArgAsnGlyAla | | 344 |

Fig. 4

5'-GTGGACGGACTGACGTAGATCAAGGTTGCG-3'

Fig. 5

5'-ATGCATCTTTCCCGTTCGCGCCCTCCGGTT-3'

ALCOHOL DEHYDROGENASE GENE OF ACETIC ACID BACTERIUM

FIELD OF THE INVENTION

The present invention relates to a gene encoding a protein having a growth-promoting function derived from a microorganism, a microorganism wherein the number of copies of such gene is amplified, particularly acetic acid bacteria belonging to the genus *Acetobacter* or the same belonging to the genus *Gluconacetobacter*, and a method for efficiently producing vinegar containing acetic acid at a high concentration using these microorganisms.

BACKGROUND OF THE INVENTION

Acetic acid bacteria are microorganisms broadly utilized for vinegar production. In particular, acetic acid bacteria belonging to the genus *Acetobacter* or the same belonging to the genus *Gluconacetobacter* are utilized for industrial acetic acid fermentation.

In acetic acid fermentation, ethanol in media is oxidized and converted into acetic acid by acetic acid bacteria, and as a result, acetic acid is accumulated in the media. However, acetic acid has an inhibitory action on acetic acid bacteria. As the amount of accumulated acetic acid increases and the acetic acid concentration in media becomes higher, the growth ability and the fermentation ability of acetic acid bacteria gradually decrease.

In particular, growth induction period, that is, the period until acetic acid bacteria actually start to grow, and then it becomes possible to confirm the accumulation of acetic acid, tends to be longer as acetic acid concentration becomes higher.

Hence, in acetic acid fermentation, it is desired to further shorten the growth induction period, even in the case of a high acetic acid concentration. As a means for this purpose, a method has been reported that involves adding PQQ (4,5-dihydro-4,5-dioxo-1H-pyrrolo [2,3-f] quinoline-2,7,9-tricarboxylic acid) to a fermentation liquid to promote growth, so as to shorten so-called the growth induction period (e.g., see Patent document 1).

However, obtainment of PQQ in large quantities is difficult and PQQ is expensive. Thus, implementation of such a method at industrial scale is always associated with problems. Accordingly, it has been attempted to breed and improve acetic acid bacteria by promoting the growth of acetic acid bacteria, cloning genes (growth-promoting genes) encoding proteins having a function capable of shortening so-called the growth induction period, and using the growth-promoting genes.

However, no genes involved in growth promotion of acetic acid bacteria have been isolated so far. Under such circumstances, isolation of a novel growth-promoting gene encoding a protein having a function of promoting the growth of acetic acid bacteria at practical level and of shortening the growth induction period and breeding of acetic acid bacteria having a stronger growth function using the growth-promoting gene have been desired.

Patent document 1: JP Patent Publication (Kokai) No. 61-58584 A (1986)
Patent document 2: JP Patent Publication (Kokai) No. 60-9488 A (1985)
Patent document 3: JP Patent Publication (Kokai) No. 60-9489 A (1985)
Patent document 4: Specification of JP Patent Application No. 2003-350265

Non-patent document 1: "Biochimica et Biophysica Acta," vol. 1088, pp. 292-300, 1991
Non-patent document 2: "Applied and Environmental Microbiology," vol. 55, pp. 171-176, 1989
Non-patent document 3: "Agricultural and Biological Chemistry," vol. 52, pp. 3125-3129, 1988
Non-patent document 4: "Agricultural and Biological Chemistry," vol. 49, pp. 2091-2097, 1985
Non-patent document 5: "Bioscience, Biotechnology and Biochemistry," vol. 58, pp. 974-975, 1994
Non-patent document 6: "European Journal of Biochemistry," vol. 254, pp. 356-362, 1998
Non-patent document 7: "Methods in Enzymology," vol. 89, pp. 450-457, 1982
Non-patent document 8: "Methods in Enzymology," vol. 89, pp. 491-496, 1982
Non-patent document 9: "Cellulose," pp. 153-158, 1989

SUMMARY OF THE INVENTION

As described above, no successful relevant cases have been reported, such as elucidation of the growth-promoting function of acetic acid bacteria at the gene level or development of practical acetic acid bacteria having a high growth-promoting function. Hence, the objects of the present invention are to isolate a novel alcohol dehydrogenase gene encoding a protein capable of improving the growth-promoting function at practical level, breed an acetic acid bacterium having a better growth-promoting function using the alcohol dehydrogenase gene, and provide a method for efficiently producing vinegar with a higher acetic acid concentration using the acetic acid bacterium.

We generated a hypothesis that a specific growth-promoting gene (that is absent in other microorganisms) is present in acetic acid bacteria, which are capable of growing and fermenting even in the presence of acetic acid. We then conceived the novel idea that the use of such a gene would enable further improvement in the growth-promoting function of microorganisms than ever before, and would enable development of a method for producing vinegar containing acetic acid at a high concentration more efficiently than ever before. Thus, we have completed the present invention.

The present invention is as follows.

(1) A protein ADH, which is either of the following (A) or (B):
  (A) a protein ADH, which has the amino acid sequence represented by SEQ ID NO: 2; or
  (B) a protein ADH, which consists of an amino acid sequence derived from the amino acid sequence represented by SEQ ID NO: 2 by substitution, deletion, insertion, addition, or inversion of 1 or several amino acids and has alcohol dehydrogenase activity.

(2) The DNA of a gene, which encodes either of the following protein ADH (A) or (B):
  (A) a protein ADH, which has the amino acid sequence represented by SEQ ID NO: 2; or
  (B) a protein ADH, which consists of an amino acid sequence derived from the amino acid sequence represented by SEQ ID NO: 2 by substitution, deletion, insertion, addition, or inversion of 1 or several amino acids and has alcohol dehydrogenase activity.

(3) A gene, which consists of the following DNA (A), (B), or (C):
  (A) a DNA, which contains the nucleotide sequence consisting of nucleotide Nos. 359 to 1390 within the nucleotide sequence represented by SEQ ID NO: 1, (B) a DNA, which hybridizes under stringent conditions to a DNA consisting of a nucleotide sequence complementary to the DNA consisting of the nucleotide sequence of nucleotide Nos. 359 to 1390 within the nucleotide sequence represented by SEQ ID NO: 1 and encodes a protein ADH having alcohol dehydrogenase activity; or (C) a DNA, which hybridizes under stringent conditions to a DNA consisting of a nucleotide sequence that can be a probe prepared from a part of the DNA consisting of the nucleotide sequence of nucleotide Nos. 359 to 1390 within the nucleotide sequence represented by SEQ ID NO: 1 and encodes the protein ADH having alcohol dehydrogenase activity.

(4) A recombinant vector, which contains the DNA of (2) or (3).

(5) A transformant, which contains the recombinant vector of (4).

(6) A microorganism, which has alcohol dehydrogenase activity enhanced by an amplified number of copies of the DNA of (2) or (3) within a cell.

(7) The microorganism of (6), which is an acetic acid bacterium belonging to the genus *Acetobacter* or the genus *Gluconacetobacter*.

(8) A method for producing vinegar, which comprises culturing the microorganism of (6) or (7) in a medium containing alcohol and causing the microorganism to produce and accumulate acetic acid in the medium.

(9) Vinegar containing acetic acid at a high concentration, which is obtained by the method of (8).

(10) The vinegar of (9), wherein the acetic acid concentration ranges from 10% to 13%.

According to the present invention, it is possible to impart a growth-promoting function to microorganisms and enhance the function. Furthermore, to microorganisms having ability to oxidize alcohol, particularly to acetic acid bacteria, ability to significantly shorten the growth induction period and efficiently accumulate acetic acid at a high concentration in a medium can be imparted.

The present invention is explained in detail as follows. This application claims a priority of Japanese patent application No. 2003-66697 filed on Mar. 12, 2003, and encompasses the content described in the specification and/or drawings of the Japanese patent application.

As a result of intensive studies concerning a method for discovering a growth-promoting gene from acetic acid bacteria, we have developed a method for isolating a growth-promoting gene from acetic acid bacteria by constructing a chromosomal DNA library of an acetic acid bacterium, transforming the chromosomal DNA library into acetic acid bacteria, and then screening for a gene that enables a strain to grow within 3 days on agar media in the presence of 1% acetic acid, whereas the strain generally requires 4 days to grow on the same media.

By the use of this method, we have succeeded for the first time in cloning a novel alcohol dehydrogenase gene (hereinafter it may also be referred to as the adh gene) capable of improving the growth-promoting function at a practical level from acetic acid bacteria belonging to the genus *Gluconacetobacter*, which are actually used for vinegar production.

The thus obtained adh gene has homology to some extent with a group of proteins produced by an adhP gene that has been discovered in *Escherichia coli*, an adh A gene in *Shinorhizobium meliloti* and the like, as a result of homology search of DDBJ/EMBL/Genbank and SWISS-PROT/PIR. It was inferred that the adh gene is an alcohol dehydrogenase gene (adh gene) of acetic acid bacteria.

However, the adh gene of the present invention has extremely low homology of 6.4% at the amino acid sequence level with an adh gene (e.g., see Non-patent document 1) of an acetic acid bacterium (*Acetobacter polyoxogenes*) that has been reported so far. Moreover, the predicted molecular weight of the adh gene of the present invention differs greatly from that of the adh gene as reported in Non-patent document 1. Hence, it has been confirmed that the adh gene of the present invention clearly differs from that of any adh gene as a membrane protein that has been reported to date.

Furthermore, the adh gene of the present invention has 39% homology at the amino acid sequence level with the adhP gene of *Escherichia coli* and has 56% homology at the amino acid sequence level with the adhA gene of *Shinorhizobium meliloti*. Because of such extremely low degrees of homology, it was confirmed that the adh gene of the present invention is somewhat similar to adh genes of other prokaryotes, but is a novel gene encoding a novel protein (also referred to as protein ADH) specific to acetic acid bacteria.

In the present invention, a transformant having an amplified number of copies of the adh gene was prepared by ligating the adh gene to a plasmid vector and then transforming an acetic acid bacterium with the vector. It was confirmed that the gene encodes a protein having alcohol dehydrogenase activity of the acetic acid bacterium, because alcohol dehydrogenase activity is enhanced by approximately 54 times in the transformant.

We have also discovered that when aeration culture is carried out in the presence of ethanol, acetic acid fermentation ability, particularly a growth-promoting function, is significantly improved, and the growth induction period is shortened. Therefore, vinegar with a high acetic acid concentration can be efficiently produced. Thus, we have completed the present invention.

The present invention will be described in detail as follows.

(1) DNA of the present invention

The DNA of the present invention has homology to some extent with an adh gene of *Escherichia coli* or the like and contains a nucleotide sequence that can encode alcohol dehydrogenase having the amino acid sequence represented by SEQ ID NO: 2 in the sequence listing, which can improve the growth-promoting function. The DNA of the present invention contains regulatory element and structural gene.

The DNA of the present invention can be obtained from the chromosomal DNA of *Gluconacetobacter entanii* as described below.

First, a chromosomal DNA library of *Gluconacetobacter entanii*, such as the *Acetobacter altoacetigenes* MH-24 strain (deposited under accession number FERM BP-491 on Feb. 23, 1984, (original deposition) with the International Patent Organism Depositary (Tsukuba Central 6, 1-1-1 Higashi, Tsukuba, Ibaraki, Japan), the National Institute of Advanced Industrial Science and Technology (AIST)), is prepared. In addition, the chromosomal DNA is obtained by a conventional method (e.g., see Patent document 3).

Next, to isolate an alcohol dehydrogenase gene from the obtained chromosomal DNA, a chromosomal DNA library is constructed. First, the chromosomal DNA is partially digested with appropriate restriction enzymes to obtain a mixture of various fragments. Through the regulation of time for cleavage reaction and the like so as to regulate the degrees of cleavage, wide-ranging types of restriction enzymes can be used. For example, the chromosomal DNA is digested by causing Satu3A I to act on the DNA at 30° C. or more, preferably at 37° C., at enzyme concentration ranging from 1 to 10 units/ml for various reaction time (1 minute to 2 hours). In addition, Pst I was used in Examples shown below.

Next, the thus cleaved chromosomal DNA fragment is ligated to a vector DNA that is autonomously replicable within acetic acid bacteria, thereby constructing a recombinant vector. Specifically, a restriction enzyme (such as Pst I, which causes the generation of a terminal nucleotide sequence complementary to the restriction enzyme Pst I used for the cleavage of the chromosomal DNA) is caused to act on the vector DNA under conditions of 37° C. and enzyme concentration ranging from 1 to 100 units/ml for 1 or more hours, thereby completely digesting and cleaving the vector DNA.

Next, the above-obtained mixture of chromosomal DNA fragments is mixed with the cleaved vector DNA, and then $T_4$ DNA ligase is caused to act thereon under conditions in which temperature ranges from 4° C. to 16° C. and enzyme concentration ranges from 1 to 100 units/ml for 1 or more hours (preferably 6 to 24 hours), thereby obtaining a recombinant vector.

An acetic acid bacterium that generally requires 4 days to grow in the presence of 1% acetic acid concentration on agar medium, such as the *Acetobacter aceti* No. 1023 strain (deposited under accession number FERM BP-2287 on Jun. 27, 1983, (original deposition) with the National Institute of Advanced Industrial Science and Technology, the International Patent Organism Depositary (Tsukuba Central 6, 1-1-1 Higashi, Tsukuba, Ibaraki, Japan)) is transformed using the thus obtained recombinant vector. Subsequently, the resultant is spread on agar medium containing 1% acetic acid, followed by 3 days of culture. The generated colonies are inoculated and cultured in liquid medium. Plasmids are collected from the thus obtained bacterial cells, so that DNA fragments containing the adh gene can be obtained.

A specific example of the DNA of the present invention the nucleotide sequence of SEQ ID NO: 1 in the sequence listing. In such DNA, a nucleotide sequence consisting of nucleotide Nos. 359 to 1390 is a coding region.

Figure 3:
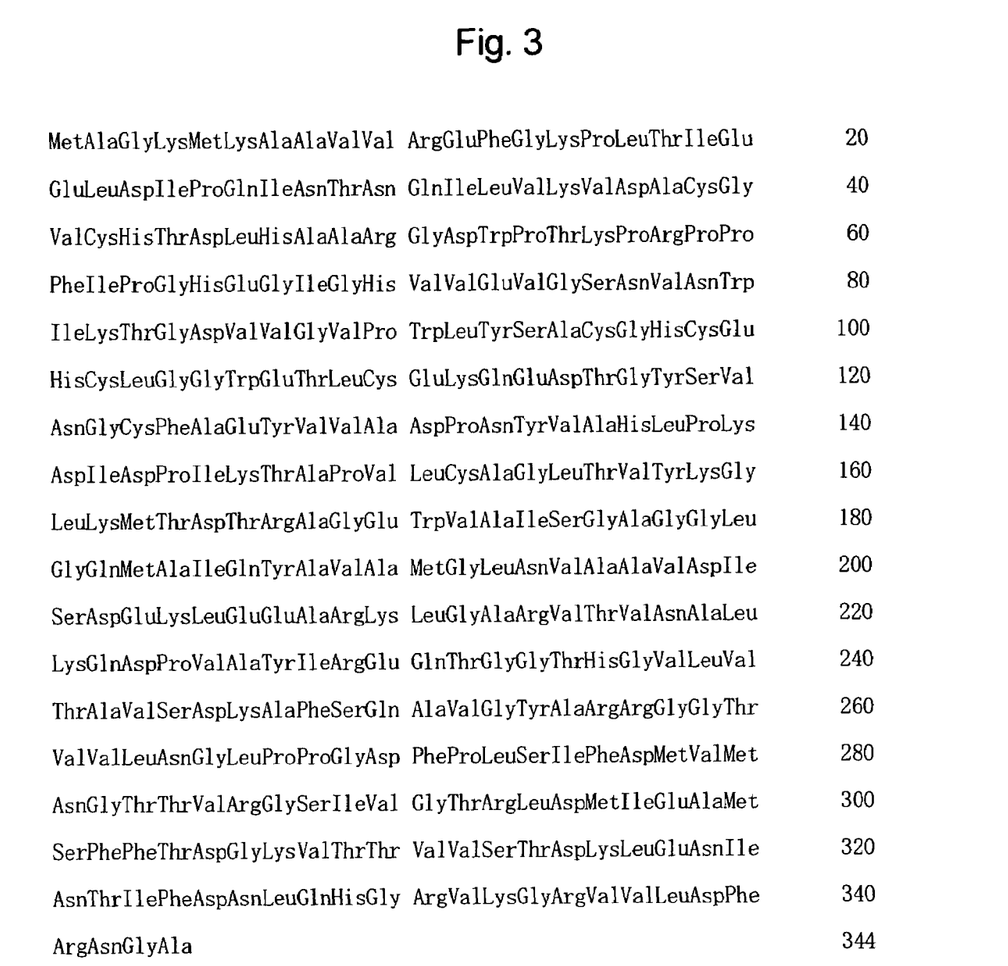
FIG. 3 shows the amino acid sequence (SEQ ID NO: 2) of a protein encoded by the NAD-dependent alcohol dehydrogenase gene derived from *Gluconacetobacter entanii*.

The nucleotide sequence represented by SEQ ID NO: 1 in the sequence listing or the amino acid sequence represented by SEQ ID NO: 2 (corresponding to FIG. 3: nucleotide Nos. 359 to 1390) in the sequence listing showed 39% homology at the amino acid sequence level with the adhP gene of *Escherichia coli* and showed 56% homology at the amino acid sequence level with the adhA gene of *Shinorhizobium moliloti* as a result of homology search of DDBJ/EMBL/Genbank and SWISS-PROT/PIR. Thus, it was inferred that the relevant gene encodes a protein ADH. However, because both homologies were as low as 60% or less, it was clear that the gene is a novel gene differing from these genes.

Furthermore, obtainment of an adh gene from acetic acid bacterium, *Acetobacter polyoxogenes*, has been reported (e.g., see Non-patent document 1). Amino acid sequence homology between the protein encoded by the adh gene in this case and the protein encoded by the nucleotide sequence consisting of nucleotide Nos. 359 to 1390 is as very low as 6.4%. The gene of the present invention clearly differs from known adh genes and is clearly a novel adh gene of acetic acid bacteria.

The nucleotide sequence of the DNA of the present invention has been clarified. Thus, the DNA can be obtained by, for example, polymerase chain reaction (PCR reaction) using genome DNA of an acetic acid bacterium, *Gluconacetobacter entanii*, as a template, and oligonucleotides synthesized based on the nucleotide sequence, as primers, or by hybridization using an oligonucleotide synthesized based on the nucleotide sequence as a probe.

Oligonucleotides can be synthesized according to a conventional method using, for example, various commercially available DNA synthesizers. Furthermore, PCR reaction can be carried out according to a conventional method using the Thermal Cycler Gene Amp PCR system 9700 produced by Applied Biosystems, Taq DNA polymerase (produced by TAKARA BIO INC.), KOD-Plus- (produced by TOYOBO CO., LTD.), and the like.

The DNA of the present invention encoding the protein ADH having a growth-promoting function may be any DNA that encodes a protein obtained by deletion, substitution, insertion, or addition or inversion of 1 or several amino acids at 1 or a plurality of positions, as long as the alcohol dehydrogenase activity or the growth-promoting function of the protein ADH to be encoded is not deteriorated.

Such a DNA encoding a protein ADH substantially identical to alcohol dehydrogenase having a growth-promoting function can be obtained also by, for example, site-directed mutagenesis, specifically by altering the nucleotide sequence by deletion, substitution, insertion, or addition or inversion of amino acids at specific sites. Moreover, the above-altered DNA can also be obtained by a conventionally known treatment to cause mutation.

Furthermore, it is generally known that the amino acid sequence of a protein and the nucleotide sequence encoding the protein differ slightly between species, strains, variants, and varieties. DNAs encoding substantially identical proteins can be obtained from overall acetic acid bacteria, particularly those of species, strains, variants, and varieties of the genus *Acetobacter* or the genus *Gluconacetobacter*.

Specifically, a DNA that hybridizes under stringent conditions to, for example, a DNA consisting of a nucleotide sequence complementary to the nucleotide sequence consisting of nucleotide Nos. 359 to 1390 (of the nucleotide sequence of SEQ ID NO: 1 in the sequence listing) or a DNA consisting of a nucleotide sequence that can be a probe prepared from a part of the nucleotide sequence consisting of nucleotide Nos. 359 to 1390 (of the nucleotide sequence of SEQ ID NO: 1 in the sequence listing); and encodes a protein having a function to enhance resistance to acetic acid is isolated from acetic acid bacteria of the genus *Acetobacter* or the genus *Gluconacetobacter*, mutated acetic acid bacteria of the genus *Acetobacter* or the genus *Gluconacetobacter*, or naturally mutated strains or varieties thereof In this way, a DNA encoding a protein substantially identical to the protein can also be obtained. The term "stringent conditions" used herein means conditions whereby so-called specific hybrids are formed and non-specific hybrids are not formed. It is difficult to precisely represent such conditions in numerical values. Examples of such conditions include conditions wherein nucleotide sequences sharing high homology, for example, DNAs sharing 70% or more homology, hybridize to each other and nucleotide sequences sharing homology lower than this level do not hybridize to each other. Other such examples include general washing conditions for hybridization, such as conditions wherein washing is carried out at 60° C. with a salt concentration corresponding to 0.1% SDS in the case of 1×SSC.

(2) Acetic acid bacteria in the present invention Acetic acid bacteria in the present invention are belonging to the genus *Acetobacter* or to the genus *Gluconacetobacter*, both of which have enhanced resistance to acetic acid.

Specific examples of bacteria of the genus *Acetobacter* include *Acetobacter aceti* such as the *Acetobacter aceti* No. 1023 strain (deposited with the International Patent Organism Depositary under FERM BP-2287), the *Acetobacter aceti* subsp. *xylinum* IFO3288 strain, and the *Acetobacter aceti* IFO3283 strain.

Furthermore, examples of bacteria of the genus *Gluconacetobacter* include the *Gluconacetobacter europaeus* DSM6160 strain and *Gluconacetobacter entanii* such as *Acetobacter altoacetigenes*. MH-24 strain that is currently deposited with the International Patent Organism Depositary under FERM BP-491.

The growth-promoting function is enhanced by, for example, amplifying the number of copies of the adh gene within the cells or transforming bacteria of the genus *Acetobacter* using recombinant DNA obtained by ligating a DNA fragment containing the structural gene to a promoter sequence that efficiently functions in bacteria of the genus *Acetobacter*.

The growth-promoting function can also be enhanced by substituting a promoter sequence of the gene on a chromosomal DNA with another promoter sequence that efficiently functions in acetic acid bacteria of the genus *Acetobacter* or the genus *Gluconacetobacter*. Examples include a promoter sequence derived from a microorganism other than acetic acid bacteria, such as a promoter of each gene of an ampicillin resistance gene of a plasmid pBR322 (produced by TAKARA BIO INC.) of *Escherichia coli*, a kanamycin resistance gene of a plasmid pHSG298 (produced by TAKARA BIO INC.), a chloramphenicol resistance gene of a plasmid pHSG396 (produced by TAKARA BIO INC.), and a β-galactosidase gene.

The number of copies of the gene within the cells can be amplified by introducing a multi-copy vector retaining the gene into cells of acetic acid bacteria of the genus *Acetobacter*. Specifically, amplification can also be carried out by introducing a plasmid retaining the gene, a transposon retaining the gene, or the like into cells of acetic acid bacteria of the genus *Acetobacter* or the genus *Gluconacetobacter*.

Examples of a multi-copy vector (acetic acid bacterium-*Escherichia coli* shuttle vector) include pMV24 (e.g., see Non-patent document 2), pGI18 (e.g., see Patent document 4), pUF106 (e.g., see Non-patent document 9), pTA5001 (A), and pTA5001 (B) (e.g., see Patent document 2). Another example of this is pMVLI (e.g., see Non-patent document 3), which is a chromosomal integrating vector. Furthermore, examples of a transposon include Mu and IS1452.

DNA can be introduced into acetic acid bacteria of the genus *Acetobacter* or the genus *Gluconacetobacter* by a calcium chloride method (e.g., see Non-patent document 4), an electroporation method (e.g., see Non-patent document 5), or the like.

A transformant is obtained by introducing a recombinant plasmid into *Acetobacter aceti* No. 1023 (FERM BP-2287). Such a recombinant plasmid comprises at least a DNA fragment having the nucleotide sequence represented by SEQ ID NO: 1 in the sequence listing, such as a recombinant plasmid pADH1 prepared by inserting the above DNA fragment into an acetic acid bacterium-*Escherichia coli* shuttle vector (multi-copy vector) pMV24.

When alcohol dehydrogenase activity is enhanced as described above in acetic acid bacteria of the genus *Acetobacter* or the genus *Gluconacetobacter* having ability to oxidize alcohol, the growth-promoting function is enhanced and the growth induction period is shortened, so that vinegar containing acetic acid at a high concentration can be efficiently produced.

(3) Method for producing vinegar Acetic acid bacteria of the genus *Acetobacter* or the genus *Gluconacetobacter* having a selectively enhanced growth-promoting function are obtained through the above-described amplification of the number of copies of the adh gene. Such acetic acid bacteria having ability to oxidize alcohol are cultured in a medium containing alcohol and then caused to produce and accumulate acetic acid in the medium, so that vinegar containing acetic acid at a high concentration can be efficiently produced.

Acetic acid fermentation in the production method of the present invention may be carried out in a manner similar to that used in a conventional vinegar production by fermentation using acetic acid bacteria. A medium to be used for acetic acid fermentation may be either a synthetic or a natural medium as long as it contains carbon sources, nitrogen sources, inorganic substances, and ethanol, and, if necessary, contains appropriate amounts of nutrition sources required for the growth of the employed microbial strain.

Examples of carbon sources include various carbohydrates such as glucose, sucrose and various organic acids. As nitrogen sources, natural nitrogen sources such as peptone and decomposed products of the fermentation microorganisms can be used.

Furthermore, culture is carried out under aerobic conditions such as those of a static culture method, a shaking culture method, and an aeration and agitation culture method. Culture is carried out at a temperature ranging from 20° C. to 40° C., preferably 25° C. to 35° C., and generally at 30° C. pH of a medium generally ranges from 2.5 to 7 and preferably ranges from 2.7 to 6.5. pH can also be adjusted using various acids, various nucleotides, buffers, and the like. Generally by 1 to 21 days of culture, acetic acid is accumulated at a high concentration in the medium. The acetic acid concentration of vinegar achieved by the use of this method ranges from 10% to 13%.

DETAILED DESCRIPTION OF THE PREFERRED EMBODIMENTS

The present invention will be further described specifically by referring to examples.

EXAMPLE 1

Cloning of a Gene Having Growth-Promoting Function from *Gluconacetobacter entanii* and Determination of the Nucleotide Sequence and the Amino Acid Sequence thereof (1) Construction of Chromosomal DNA Library The *Acetobacter altoacetigenes* MH-24 strain (FERM BP-49 1), which is a strain of *Gluconacetobacter entanii*, was cultivated in shaking culture in YPG medium (3% glucose, 0.5% yeast extract, and 0.2% polypeptone) supplemented with 6% acetic acid and 4% ethanol at 30° C. After the cultivation, the culture medium was centrifuged (7,500×g for 10 minutes), thereby obtaining bacterial cells. From the thus obtained bacterial cells, chromosomal DNAs were prepared by a chromosomal DNA preparation method (e.g., see Patent document 3).

The above-obtained chromosomal DNAs were partially digested with a restriction enzyme Pst I (produced by TAKARA BIO INC.). *Escherichia coi*-acetic acid bacterium shuttle vector pMV24 was completely digested with the restriction enzyme Pst I. Appropriate amounts of these DNAs were mixed in and then ligated using a ligation kit (TaKaRa DNA Ligation Kit Ver. 2, produced by TAKARA BIO INC.), thereby constructing a chromosomal DNA library of *Gluconacetobacter entanii*.

(2) Cloning of a gene having growth-promoting function

Figure 1:
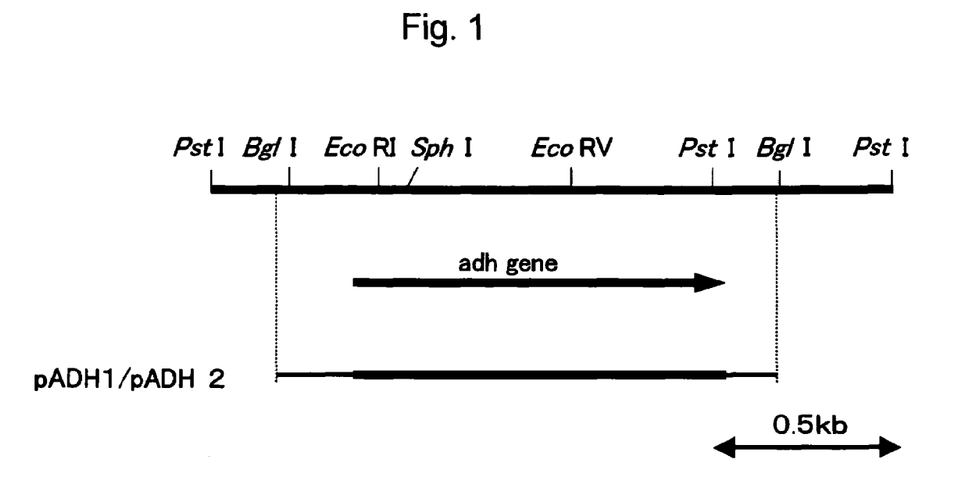
FIG. 1 is a schematic diagram of the restriction enzyme map of the gene fragment (pP1) derived from *Gluconacetobacter entanii*.

The chromosomal DNA library of *Gluconacetobacter entanii* obtained as described above was transformed into *Acetobacter aceti* No. 1023 strain that generally requires 4 days to grow on agar medium containing 1% acetic acid, and then cultured on YPG agar medium containing 1% acetic acid and 100 μg/ml ampicillin at 30° C. for 3 days. Colonies generated within 3 days were inoculated and cultured on YPG medium containing 100 μg/ml ampicillin and then plasmids were collected from the obtained bacterial cells. An approximately 1.7-kbp Pst I fragment was cloned as shown in FIG. 1, and the plasmid was named pP1. Furthermore, it could be confirmed that a fragment that had enabled the *Acetobacter aceti* No. 1023 strain to grow within 3 days on the YPG agar medium containing 1% acetic acid was an approximately 1.2-kbp Bgl I fragment in the approximately 1.7-kbp Pst I fragment cloned into pP1.

As described above, a gene fragment was obtained that enables the *Acetobacter aceti* No. 1023 strain to grow within 3 days on agar medium containing. 1% acetic acid, although the strain generally requires 4 days to grow on such agar medium containing 1% acetic acid.

(3) Determination of the Nucleotide Sequence of the Cloned DNA Fragment

The above cloned Pst I fragment was inserted into the Pst I site of pUC19, and then the nucleotide sequence of the fragment was determined by Sanger's dideoxy chain termination method. As a result, the nucleotide sequence of SEQ ID NO: 1 was determined. Sequencing was carried out for the entire region of both DNA strands with all the cleavage points overlapping with each other.

In the nucleotide sequence of SEQ ID NO: 1, the presence of an open reading frame encoding 344 amino acids as described in SEQ ID NO: 2 (FIG. 3) ranging from nucleotide No. 359 to nucleotide No. 1390 was confirmed.

EXAMPLE 2

Effect of Shortening the Growth Induction Period in a Transformant with a Gene Having Growth-Promoting Function Derived from *Gluconacetobacter entanii*

(1) Transformation into *Acetobacter aceti*

The above-cloned gene having the growth-promoting function derived from the *Acetobacter altoacetigenes* MH-24 strain (FERM BP-491) was amplified by the PCR method using KOD-Plus- (produced by TOYOBO CO., LTD.). The thus amplified DNA fragment was inserted into the restriction enzyme Sma I cleavage site of the acetic acid bacterium-*Escherichia coli* shuttle vector pMV24 (e.g., see Non-patent document 2), so as to prepare a plasmid pADH1.

The amplified fragment inserted in pADH1 is schematically shown in FIG. 1. FIG. 1 shows the restriction enzyme map of the *Gluconacetobacter entanii*-derived gene fragment (pP1) cloned using Pst I, the position of the gene having the growth-promoting function, and the fragment inserted into pADH1.

Figure 4:
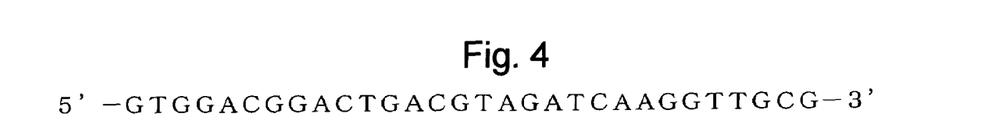
FIG. 4 shows the nucleotide sequence of primer 1 (SEQ ID NO: 3).
Figure 5:
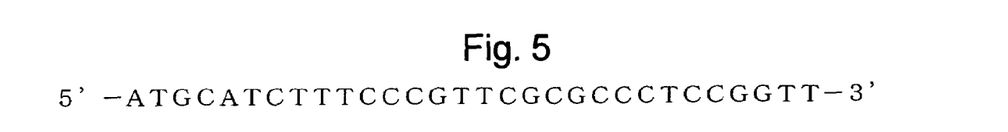
FIG. 5 shows the nucleotide sequence of primer 2 (SEQ ID NO: 4).

The PCR method was carried out as described in detail below. Specifically, PCR was carried out under the following PCR conditions using a genome DNA of the *Acetobacter altoacetigenes* MH-24 strain as a template, primer 1 (the nucleotide sequence thereof is shown in SEQ ID NO: 3 (FIG. 4)), primer 2 (the nucleotide sequence thereof is shown in SEQ ID NO: 4 (FIG. 5)), and KOD-Plus- (produced by TOYOBO CO., LTD.).

Specifically, the PCR method was carried out for 30 cycles, each of which consisted of 94° C. for 15 seconds, 60° C. for 30 seconds, and 68° C. for 1 minute.

The pADH1 was transformed into the *Acetobacter aceti* No. 1023 strain by an electroporation method (e.g., see Non-patent document 5). The transformant was selected using YPG agar medium supplemented with 100 μg/ml ampicillin and 1% acetic acid.

Plasmids were extracted from the ampicillin-resistant transformant that had grown on the selection medium within 3 days and then analyzed according to a conventional method. Thus, it was confirmed that the strain retained plasmids having the gene with the growth-promoting function.

(2) Growth-Promoting Function of the Transformant

The above-obtained ampicillin-resistant transformant having the plasmid pADH1 and the original *Acetobacter aceti* No. 1023 strain having only the shuttle vector pMV24 introduced therein were compared in terms of growth in YPG medium supplemented with acetic acid.

Specifically, shaking culture (150 rpm) was carried out at 30° C. in 100 ml of YPG medium containing 3% acetic acid, 3% ethanol, and 100 μg/ml ampicillin. The transformant and the original strain were compared in terms of growth in the medium supplemented with acetic acid by measuring absorbance at 660 nm.

Figure 2:
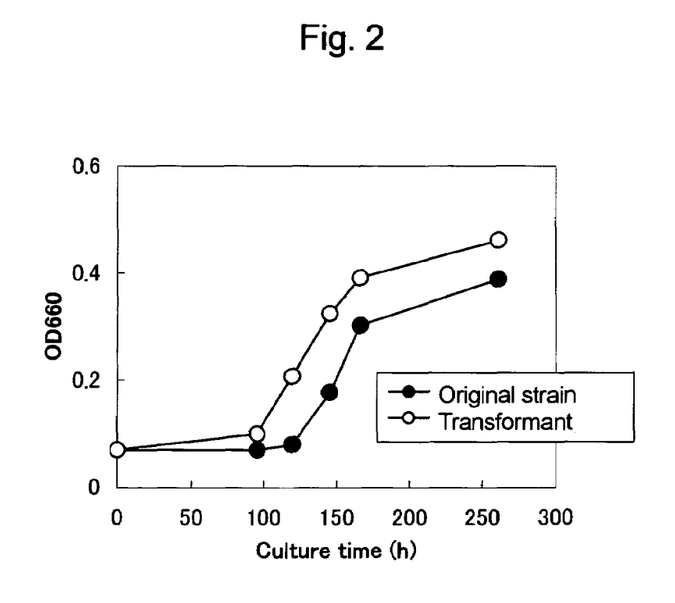
FIG. 2 shows the fermentation process of the transformant that has an amplified number of copies of the NAD-dependent alcohol dehydrogenase gene derived from *Gluconacetobacter entanii*.

As a result, as shown in FIG. 2, it could be confirmed that the transformant grew faster than the original *Acetobacter aceti* No. 1023 strain in the medium supplemented with 3% acetic acid and 3% ethanol. The effect of enhancing the growth-promoting function of the gene could be confirmed.

(3) Various Enzyme Activities of the Transformant and the Original Strain

For the ampicillin-resistant transformant having the plasmid pADH1 and the original *Acetobacter aceti* No. 1023 strain having only the shuttle vector pMV24 introduced therein, NAD-dependent alcohol dehydrogenase activity was measured with the modified method used in bacteria (e.g., see Non-patent document 6). Specifically, an appropriate amount of disrupted cell suspension was added to 1 ml of reaction mixture containing 25 mM sodium phosphate buffer (pH 7.5), 500 mM ethanol, and 1.5 mM NAD+, and then absorbance at 340 nm was measured at 25° C. The amount of 1 μmol of NADH produced per minute was determined to correspond to 1U of activity. Furthermore, membrane-bound alcohol dehydrogenase activity was measured with the method used in acetic acid bacteria (e.g., see Non-patent document 7) and membrane-bound aldehyde dehydrogenase activity was measured with the method used in acetic acid bacteria (e.g., see Non-patent document 8). The results are shown in Table 1.

TABLE 1

| | NAD-dependent alcohol dehydrogenase (U/mg) | Membrane-bound alcohol dehydrogenase (U/mg) | Membrane-bound aldehyde dehydrogenase (U/mg) |
|---|---|---|---|
| Original strain | 0.17 | 2.17 | 8.63 |
| Transformant | 9.19 | 1.82 | 7.01 |

Based on the results in Table 1, the transformant was found to have membrane-bound alcohol dehydrogenase activity and aldehyde dehydrogenase activity at the same levels as those of the original *Acetobacter aceti* No. 1023 strain. However, the transformant had NAD-dependent alcohol dehydrogenase activity that was higher by approximately 54 times than that of the original strain. Thus, it was confirmed that the cloned gene was the adh gene encoding NAD-dependent alcohol dehydrogenase.

EXAMPLE 3

Acetic Acid Fermentation Test for the Transformant with the Adh Gene Derived from *Gluconacetobacter entanii*

The ampicillin-resistant transformant having the plasmid pADH1 obtained in Example 2 and the original *Acetobacter aceti* No. 1023 strain having only the shuttle vector pMV24 were compared in terms of acetic acid fermentation ability.

Specifically, aeration and agitation culture (30° C., 400 rpm, and 0.20 vvm) was carried out using a 51 mini-jar fermentor (produced by Mitsuwa Scientific Corp.; KMJ-5A) containing 2.51 of YPG medium containing 1% acetic acid, 4% ethanol, and 100 μg/ml ampicillin. The strains were caused to ferment so as to result in an acetic acid concentration of 3%. Subsequently, each culture medium was removed while leaving 700 ml of the culture medium in the mini-jar fermentor. To the remaining 700 ml of the culture medium, 1.81 of YPG medium containing acetic acid, ethanol, and 100 μg/ml ampicillin was added. The medium was adjusted to result in 3% and 4% concentrations of acetic acid and ethanol, respectively, and then acetic acid fermentation was initiated again. Aeration and agitation culture was continued while adding ethanol to maintain 1% ethanol concentration in the media during fermentation. The transformant and the original strain were compared in terms of acetic acid fermentation ability. The results are summarized in Table 2.

TABLE 2

| | Final acetic acid concentration achieved (%) | Specific growth rate (OD660/hr) | Production rate (%/hr) | Growth induction period (hr) |
|---|---|---|---|---|
| Original strain | 9.9 | 0.0162 | 0.071 | 54.4 |
| Transformant | 10.5 | 0.0116 | 0.089 | 5.0 |

Based on the results in Table 2, the growth induction period was significantly shortened in the transformant compared with the case of the original strain. Thus, it could be confirmed that the transformant was able to carry out acetic acid fermentation efficiently.

EXAMPLE 4

Acetic Acid Fermentation Test for the Transformant with the Adh Gene Derived from *Gluconacetobacter entanii*

(1) Transformation into *Acetobacter altoacetigenes*

The gene having the growth-promoting function derived from the *Acetobacter altoacetigenes* MH-24 strain (FERM BP-491) was amplified by the PCR method using KOD-Plus- (produced by TOYOBO CO., LTD.). After cleavage of the acetic acid bacterium-*Escherichia coli* shuttle vector pGI18 (e.g., see Patent document 4) with the restriction enzyme Smia I, the thus amplified DNA fragment was inserted into the site, so as to prepare a plasmid pADH2. The amplified fragment inserted into pADH2 is schematically shown in FIG. 1. FIG. 1 shows the restriction enzyme map of the *Gluconacetobacter entanii*-derived gene fragment (pP1) cloned using Pst I, the position of the gene having the growth-promoting function, and the fragment inserted into pADH2.

The PCR method was carried out as described in detail below. Specifically, PCR was carried out under the following PCR conditions using a genome DNA of the *Acetobacter altoacetigenes* MH-24 strain as a template, primer 1 (the nucleotide sequence thereof is shown in SEQ ID NO: 3 (FIG. 4)), and primer 2 (the nucleotide sequence thereof is shown in SEQ ID NO: 4 (FIG. 5)), and KOD-Plus- (produced by TOYOBO CO., LTD.).

Specifically, the PCR method was carried out for 30 cycles, each of which consisted of 94° C. for 15 seconds, 60° C. for 30 seconds, and 68° C. for 1 minute.

The pADH2 was transformed into the *Acetobacter altoacetigenes* MH-24 strain by the electroporation method (e.g., see Non-patent document 5). The transformant was selected using YPG agar medium supplemented with 100 μg/ml ampicillin, 4% acetic acid, and 3% ethanol.

Plasmids were extracted from the ampicillin-resistant transformant that had grown on the selection medium and then analyzed according to a conventional method. Thus, it was confirmed that the transformant retained plasmids having the adh gene.

(2) Acetic acid fermentation test for the transformant

The ampicillin-resistant transformant having the plasmid pADH2 obtained in (1) and the original *Acetobacter altoacetigenes* MH-24 strain having only the shuttle vector pGI18 introduced therein were compared in terms of acetic acid fermentation ability.

Specifically, aeration and agitation culture (30° C., 500 rpm, and 0.20 vvm) was carried out using a 5 mini-jar fermentor (produced by Mitsuwa Scientific Corp.; KMJ-5A) containing 2.5 of raw-material medium (7% acetic acid, 3% ethanol, 0.2% yeast extract, and 0.2% glucose) containing 100 μg/ml ampicillin. At the stage where the growth of the bacteria was clearly observed and the residual ethanol concentration reached 2%, ethanol-containing medium (1% acetic acid, 50% ethanol, 0.2% yeast extract, and 0.2% glucose) was fed so that the ethanol concentration of the fermentation liquid was controlled to be 2%. With this method for acetic acid fermentation, acetic acid fermentation ability was compared between the transformant and the original strain. The results are summarized in Table 3.

TABLE 3

| | Final acetic acid concentration achieved (%) | Specific growth rate (OD660/hr) | Production rate (%/hr) |
|---|---|---|---|
| Original strain | 15.6 | 0.0061 | 0.31 |
| Transformant | 17.3 | 0.0045 | 0.17 |

Based on the results in Table 3, it could be confirmed that the transformant was significantly superior to the original strain in terms of the final acetic acid concentration achieved.

EXAMPLE 5

Acetic Acid Fermentation Test for the Transformant with the Adh Gene Derived from *Gluconacetobacter entanii*

(1) Transformation into *Acetobacter aceti* subsp. *xylinum*

The plasmid pADH2 obtained in Example 4 was transformed into the *Acetobacter aceti* subsp. *xylinum* IFO3288 strain that is a strain of *Acetobacter aceti* subsp. *xylinum* by the electroporation method (see Non-patent document 5). The transformant was selected using YPG agar medium supplemented with 100 μg/ml ampicillin.

Plasmids were extracted from the ampicillin-resistant transformant that had grown on the selection medium and then analyzed according to a conventional method. Thus, it was confirmed that the strain retained plasmids having the gene involved in enhanced resistance to acetic acid.

(2) Acetic acid fermentation test

The ampicillin-resistant transformant having the plasmid pADH2 obtained in (1) and the original *Acetobacter aceti* subsp. *xylinum* IFO3288 strain having only the shuttle vector pGI18 introduced therein were compared in terms of acetic acid fermentation ability.

Specifically, aeration and agitation culture (30° C., 500 rpm, and 0.20 vvm) was carried out in a raw-material medium (alcohol concentration of 7.8% and acetic acid concentration of 0.26%) that had been prepared by mixing 17.9% saccharified rice solution, 3.2% fermented moromi, 7.8% alcohol, and 71.1% water in a 5 l mini-jar fermentor (produced by Mitsuwa Scientific Corp.; KMJ-5A). Continuous fermentation was carried out at acetic acid concentration of 7.3%. The strains in continuous fermentation at acetic acid concentration of 7.2% were compared in terms of the raw-material medium addition rate. The results are shown in Table 4. Furthermore, the strains were compared in terms of acetic acid fermentation ability, where the raw-material medium addition rate of the transformant had been adjusted to the raw-material medium addition rate of the original strain in continuous fermentation at acetic acid concentration of 7.3%. The results are shown in Table 4.

TABLE 4

| | Acetic acid concentration (%) | OD660 | Raw-material medium addition rate (g/hr) |
|---|---|---|---|
| Original strain | 7.17 | 0.538 | 84.7 |
| Transformant | 7.20 | 0.562 | 95.5 |

TABLE 5

| | Acetic acid concentration (%) | OD660 | Raw-material medium addition rate (g/hr) |
|---|---|---|---|
| Original strain | 7.31 | 0.529 | 87.3 |
| Transformant | 7.82 | 0.466 | 88.3 |

Based on the results in Table 4 and Table 5, it could be confirmed that the transformant was significantly superior to the original strain in terms of continuous acetic acid fermentation, productivity (raw-material medium addition rate), and concentration of the produced acetic acid.

All publications, patents, and patent applications cited herein are incorporated herein by reference in their entirety.

INDUSTRIAL APPLICABILITY

According to the present invention, a novel gene involved in acetic acid resistance is provided. Furthermore, a bred strain capable of producing at high efficiency vinegar with a higher acetic acid concentration can be obtained using the gene. Thus, a method for producing at high efficiency vinegar with a higher acetic acid concentration using the bred strain can be provided.

Sequence Listing Free Text
  SEQ ID NO: 3: primer
  SEQ ID NO: 4: primer

The invention claimed is:

1. An isolated DNA wherein, said DNA encodes the protein alcohol dehydrogenase (ADH), which has the amino acid sequence of SEQ ID NO: 2.

2. An isolated nucleic acid, which comprises the nucleotide sequence consisting of nucleotide Nos: 359-1390 of SEQ ID NO: 1.

3. A recombinant vector, which contains the DNA of claim 1 or 2.

4. An isolated transformed cell, which contains the recombinant vector of claim 3.

5. A microorganism, which has alcohol dehydrogenase activity enhanced by an amplified number of copies of the DNA of claim 1 or 2 within a cell.

6. The microorganism of claim 5, which is an acetic acid bacterium belonging to the genus *Acetobacter* or the genus *Gluconacetobacter*.

7. A method for producing vinegar, which comprises culturing the microorganism of claim 5 or 6 in a medium containing alcohol and causing the microorganism to produce and accumulate acetic acid in the medium.

* * * * *

SEQUENCE LISTING

<160> NUMBER OF SEQ ID NOS: 4

<210> SEQ ID NO 1
<211> LENGTH: 1658
<212> TYPE: DNA
<213> ORGANISM: Gluconacetobacter entanii

<400> SEQUENCE: 1

```
ctgcagcatt tcggcattgg cgcgtcatgg ggtgggtatg aaagccttgt gctgcccacc      60
acgggcggga tctcgcgttc gtgcctgtcg gttacgggcg cgggaccggc gtgcaggctg     120
catgtcgggc tggaagctgg cgggttgctg gtggacgatc tggcgcgtgg tctggatggc     180
```

```
atgtctgccg cccgcgcagg gcggtggacg gactgacgta gatcaaggtt gcgacggggc    240
agggatggga cacttgcccc atacacgatg cccccgtccg gccatgccgg ccgggcgggt    300
ggcgcaggga atggtggctc catggccggg gccgtgacat cggaacggaa ggtgcaagat    360
ggctggaaag atgaaggctg cggttgtacg ggaattcggc aagccgctga cgatcgagga    420
actggacatt ccgcagatca acaccaacca gatcctggtc aaggtcgatg cctgcggcgt    480
ctgccatact gacctgcatg ccgcccgtgg cgactggccc accaagccca ggccgccctt    540
tatcccgggg cacgagggaa tcggccatgt ggtcgaggtc ggcagcaacg tcaactggat    600
caagaccggc gacgtggtgg gcgtgccgtg gctgtattcg gcctgcgggc attgcgaaca    660
ctgtctgggc ggatgggaaa ccctgtgtga aaagcaggag gacaccggct attccgtcaa    720
tggctgcttt gccgaatatg tggtggccga ccccaattac gtcgcccatc tgccgaaaga    780
catcgacccg atcaagacgg ccccgtgct gtgcgcgggg ctgacggtgt acaagggcct    840
gaagatgacg gacacccggg ccggggaatg ggtcgccatt ccggcgcgg gcgggcttgg    900
gcagatggcc atccagtacg cggtggccat gggcctgaac gtggcggcgg tggatatcag    960
cgatgaaaag ctggaagaag cccgcaagct gggcgcgcgc gtgaccgtca acgcgctgaa   1020
gcaggatccg gtcgcctata tccgcgaaca gaccggcggc acccacggcg tgctggtcac   1080
cgccgtgtcg gacaaggcgt tcagccaggc ggtgggttac gcgcggcgcg gcggcacggt   1140
ggtgctgaac ggcctgccgc cggtgacttt cccgctgtcc atctttgaca tggtgatgaa   1200
tggcacgacc gtgcgcggat ccattgtcgg cacgcggctg gacatgatcg aagccatgtc   1260
cttcttcact gatggcaagg tgacgacggt ggtcagcacg gacaaactgg aaaacatcaa   1320
caccattttc gacaacctgc agcatggccg ggtaaaggga cgcgtggtgc tggatttccg   1380
taacggggcc tgaaacgacg gcagccgcca ccctgatgcc cgttcagggt ggcgtatcgt   1440
gtaaccggag ggcgcgaacg ggaaagatgc atcccgtcgt cgcgccgccg tgcaagtgg   1500
ctgtccgatg taaaacgaca gggttattgc gcattccggc taaaggatgc cgatacgatg   1560
cagtaatttt tcggacaggt gcgctatttt attgtcgggt cccggtctca ggtcggaaaa   1620
ttttattttg ggcggattga atttctttat ttctgcag                          1658
```

<210> SEQ ID NO 2
<211> LENGTH: 344
<212> TYPE: PRT
<213> ORGANISM: Gluconacetobacter entanii

<400> SEQUENCE: 2

```
Met Ala Gly Lys Met Lys Ala Ala Val Val Arg Glu Phe Gly Lys Pro
                5                   10                  15
Leu Thr Ile Glu Glu Leu Asp Ile Pro Gln Ile Asn Thr Asn Gln Ile
            20                  25                  30
Leu Val Lys Val Asp Ala Cys Gly Val Cys His Thr Asp Leu His Ala
        35                  40                  45
Ala Arg Gly Asp Trp Pro Thr Lys Pro Arg Pro Pro Phe Ile Pro Gly
    50                  55                  60
His Glu Gly Ile Gly His Val Val Glu Val Gly Ser Asn Val Asn Trp
65                  70                  75                  80
Ile Lys Thr Gly Asp Val Val Gly Val Pro Trp Leu Tyr Ser Ala Cys
                85                  90                  95
Gly His Cys Glu His Cys Leu Gly Gly Trp Glu Thr Leu Cys Glu Lys
            100                 105                 110
```

```
Gln Glu Asp Thr Gly Tyr Ser Val Asn Gly Cys Phe Ala Glu Tyr Val
        115                 120                 125

Val Ala Asp Pro Asn Tyr Val Ala His Leu Pro Lys Asp Ile Asp Pro
    130                 135                 140

Ile Lys Thr Ala Pro Val Leu Cys Ala Gly Leu Thr Val Tyr Lys Gly
145                 150                 155                 160

Leu Lys Met Thr Asp Thr Arg Ala Gly Glu Trp Val Ala Ile Ser Gly
                165                 170                 175

Ala Gly Gly Leu Gly Gln Met Ala Ile Gln Tyr Ala Val Ala Met Gly
            180                 185                 190

Leu Asn Val Ala Ala Val Asp Ile Ser Asp Glu Lys Leu Glu Glu Ala
        195                 200                 205

Arg Lys Leu Gly Ala Arg Val Thr Val Asn Ala Leu Lys Gln Asp Pro
    210                 215                 220

Val Ala Tyr Ile Arg Glu Gln Thr Gly Gly Thr His Gly Val Leu Val
225                 230                 235                 240

Thr Ala Val Ser Asp Lys Ala Phe Ser Gln Ala Val Gly Tyr Ala Arg
                245                 250                 255

Arg Gly Gly Thr Val Val Leu Asn Gly Leu Pro Pro Gly Asp Phe Pro
            260                 265                 270

Leu Ser Ile Phe Asp Met Val Met Asn Gly Thr Thr Val Arg Gly Ser
        275                 280                 285

Ile Val Gly Thr Arg Leu Asp Met Ile Glu Ala Met Ser Phe Phe Thr
    290                 295                 300

Asp Gly Lys Val Thr Thr Val Ser Thr Asp Lys Leu Glu Asn Ile
305                 310                 315                 320

Asn Thr Ile Phe Asp Asn Leu Gln His Gly Arg Val Lys Gly Arg Val
                325                 330                 335

Val Leu Asp Phe Arg Asn Gly Ala
            340

<210> SEQ ID NO 3
<211> LENGTH: 30
<212> TYPE: DNA
<213> ORGANISM: Artificial sequence
<220> FEATURE:
<223> OTHER INFORMATION: PCR primer targeted to the Acetobacter
      altoacetigenes MH-24 strain

<400> SEQUENCE: 3
gtggacggac tgacgtagat caaggttgcg                                     30

<210> SEQ ID NO 4
<211> LENGTH: 30
<212> TYPE: DNA
<213> ORGANISM: Artificial sequence
<220> FEATURE:
<223> OTHER INFORMATION: PCR primer targeted to the Acetobacter
      altoacetigenes MH-24 strain

<400> SEQUENCE: 4
atgcatcttt cccgttcgcg ccctccggtt                                     30
```